US010406223B2

(12) United States Patent
Shin et al.

(10) Patent No.: US 10,406,223 B2
(45) Date of Patent: Sep. 10, 2019

(54) METHODS FOR PREPARING HEPATITIS B IMMUNOGLOBULIN DERIVED FROM PLASMA

(71) Applicant: GREEN CROSS HOLDINGS CORPORATION, Youngin-si, Gyeonggi-do (KR)

(72) Inventors: Yong Won Shin, Suwon-si (KR); Dong Il Park, Cheongju-si (KR); Chung Mo Ahn, Cheongju-si (KR); Jong Kyung Kim, Cheongju-si (KR); Dong Hwee Lee, Cheongju-si (KR)

(73) Assignee: GREEN CROSS HOLDINGS CORPORATION, Youngin-si (KR)

(*) Notice: Subject to any disclaimer, the term of this patent is extended or adjusted under 35 U.S.C. 154(b) by 0 days.

(21) Appl. No.: 15/579,427

(22) PCT Filed: Jun. 2, 2016

(86) PCT No.: PCT/KR2016/005837
§ 371 (c)(1),
(2) Date: Dec. 4, 2017

(87) PCT Pub. No.: WO2016/195387
PCT Pub. Date: Dec. 8, 2016

(65) Prior Publication Data
US 2018/0140699 A1 May 24, 2018

(30) Foreign Application Priority Data
Jun. 5, 2015 (KR) .................. 10-2015-0080042

(51) Int. Cl.
| A01K 67/027 | (2006.01) |
| C07H 21/04 | (2006.01) |
| A61K 38/00 | (2006.01) |
| C07K 16/08 | (2006.01) |
| A61K 39/00 | (2006.01) |
| A61K 39/395 | (2006.01) |
| B01D 15/36 | (2006.01) |
| C07K 16/10 | (2006.01) |
| C07K 1/18 | (2006.01) |
| C07K 1/34 | (2006.01) |
| A61P 43/00 | (2006.01) |
| A61P 1/00 | (2006.01) |
| A61K 39/29 | (2006.01) |
| A61K 39/42 | (2006.01) |

(52) U.S. Cl.
CPC ........ *A61K 39/39525* (2013.01); *A61K 39/29* (2013.01); *A61K 39/395* (2013.01); *A61K 39/42* (2013.01); *A61P 1/00* (2018.01); *A61P 43/00* (2018.01); *B01D 15/36* (2013.01); *C07K 1/18* (2013.01); *C07K 1/34* (2013.01); *C07K 16/10* (2013.01); *A61K 2039/505* (2013.01)

(58) Field of Classification Search
CPC .......... A61K 2300/00; A61K 2039/505; C12N 15/8509; A01K 2227/105; A23V 2002/00
See application file for complete search history.

(56) References Cited

U.S. PATENT DOCUMENTS

| 4,124,576 A | 11/1978 | Coval |
| 4,764,309 A | 8/1988 | Decker et al. |
| 2009/0148435 A1* | 6/2009 | Lebreton .................. C07K 1/18 424/130.1 |

FOREIGN PATENT DOCUMENTS

| CN | 104001172 A | * | 8/2014 |
| CN | 104001172 A | | 8/2014 |
| CN | 104004090 A | | 8/2014 |
| CN | 104231075 A | | 12/2014 |
| DE | 26 04 759 C2 | | 6/1983 |
| JP | 6107561 A | | 4/1994 |
| JP | 2002517516 A | | 6/2002 |
| KR | 10-1983-0007083 B1 | | 10/1983 |
| KR | 10 2001 0052733 A | | 6/2001 |

OTHER PUBLICATIONS

European Patent Office; Communication dated Nov. 15, 2018 in counterpart application No. 16803742.2.
Staby, et al., "Comparison of chromatographic ion-exchange resins V. Strong and weak cation-exchange resins", Journal of Chromatography A, Elsevier, Amsterdam, NL, Jun. 23, 2006, pp. 168-179, vol. 1118, No. 2 (12 pages total).
Roberts et al., "Development of an intravenous immunoglobulin with improved safety and functional activity", Biologicals 43, Published by Elsevier Ltd., 2015 (pp. 123-129).
Laursen et al., "Development, Manufacturing and Characterization of a Highly Purified, Liquid Immunoglobulin G Preparation from Human Plasma", Transfusion Medicine and Hemotherapy, vol. 41, pp. 205 to 212, Karger, Apr. 14, 2014.
Japanese Patent Office; Communication dated Nov. 6, 2018 in counterpart Japanese application No. 2018-515746.
E.J. Cohn et al., "Preparation and Properties of Serum and Plasma Proteins. IV. A System for the Separation into Fractions of the Protein and Lipoprotein Components of Biological Tissues and Fluids", J. Am. Chem. Soc., Mar. 1946, pp. 459-475, vol. 68.

(Continued)

Primary Examiner — Barry A Chestnut
(74) Attorney, Agent, or Firm — Sughrue Mion, PLLC

(57) ABSTRACT

The present invention relates to a preparation method of a human plasma-derived hepatitis B immunoglobulin preparation. More specifically, the present invention relates to a preparation method of a human plasma-derived hepatitis B immunoglobulin preparation characterized in that plasma protein fraction II (fraction II) containing human hepatitis B immunoglobulin is dialysis concentrated and then thrombus-producing materials and impurities formed during processes are removed by anion exchange resin and cation exchange resin purification techniques. By using the preparation method of the human plasma-derived hepatitis B immunoglobulin preparation according to the present invention, the efficiency of removing impurities and thrombus-producing materials is increased and a polymer content is maintained, whereby it is possible to produce human hepatitis B immunoglobulin with stable and improved quality.

14 Claims, 2 Drawing Sheets

(56) References Cited

OTHER PUBLICATIONS

P. Kistler et al., "Large Scale Production of Human Plasma Fractions", Vox Sang, 1962, pp. 414-424, vol. 7.
A. Polson et al., "The Fractionation of Protein Mixtures by Linear Polymers of High Molecular Weight", Biochem Biophys Acta, 1964, pp. 463-475, vol. 82.
A. Polson et al., "Fractionation of Plasma with Polyethylene Glycol", Vox Sang, 1972, pp. 107-118, vol. 23.
International Search Report for PCT/KR2016/005837 dated Sep. 6, 2016.

* cited by examiner

FIG. 2

| Concentration | Vol. (mL) | IgE (ng/mL) | PKA (IU/mL) | Albumin (µg/mL) | Transferrin (µg/mL) | FXIa (TGA) mU/mL | FXIa (Chromogenic) (mU/mL) | FXI (ng/mL) | Plasminogen (ng/mL) | Fibrinogen (µg/mL) |
|---|---|---|---|---|---|---|---|---|---|---|
| Load | 539.68 | 41.27 | 0.35 | 126.55 | 260.03 | 123.90 | 623.51 | 131.27 | 601.38 | 10.89 |
| DEAE (pH6.15) | 809.52 | 23.66 | <2.00 | 0.26 | 2.48 | 77.84 | 78.02 | 72.54 | 191.27 | 0.24 |
| DEAE (pH6.15) → CM | 2134.32 | 0.60 | <2.00 | 0.05 | 0.26 | <1.56 | 41.46 | 1.67 | 28.22 | 0.02 |
| DEAE (pH5.5) | 796.00 | 25.15 | <2.00 | 1.56 | >13.5 | 83.08 | 244.52 | 77.84 | 336.77 | 7.12 |
| DEAE (pH5.5) → DEAE (pH6.15) | 1294.00 | 13.64 | <2.00 | 0.34 | >6.9 | 53.81 | 92.64 | 46.27 | 133.56 | 0.26 |
| LRV (Log Reduction Value) | | | | | | | | | | |
| DEAE (pH6.15) | | 0.07 | - | 2.51 | 1.84 | 0.02 | 0.73 | 0.08 | 0.32 | 1.48 |
| DEAE (pH6.15) → CM | | 1.24 | - | 2.88 | 2.59 | >1.3 | 0.88 | 1.30 | 0.72 | 2.24 |
| DEAE (pH5.5) | | 0.05 | - | 1.74 | - | 0.00 | 0.24 | 0.06 | 0.01 | 0.02 |
| DEAE (pH5.5) → DEAE (pH6.15) | | 0.10 | - | 2.19 | - | <0.02 | 0.45 | 0.07 | 0.27 | 1.25 |

METHODS FOR PREPARING HEPATITIS B IMMUNOGLOBULIN DERIVED FROM PLASMA

TECHNICAL FIELD

The present invention relates to a method for preparing a human plasma-derived hepatitis B immunoglobulin preparation, and more particularly to a method for preparing a human plasma-derived hepatitis B immunoglobulin preparation, which comprises: dialyzing and concentrating plasma protein fraction II containing a human plasma-derived hepatitis B immunoglobulin; removing thrombogenic substances and impurities in the process by anion exchange resin and cation exchange resin purification techniques; effectively removing a solvent and detergent added during viral inactivation; and performing nanofiltration and adding a stabilizer to increase the stability of the immunoglobulin.

BACKGROUND ART

Immunoglobulins that are plasma proteins containing antibodies against various viruses and bacteria are used as drugs to prevent or treat diseases by administration to either subjects who naturally lack antibodies or patients who are in need of artificial supplement of antibodies because of viral or bacterial diseases.

In order to use such immunoglobulins as drugs, immunoglobulins for subcutaneous or intramuscular injection have been prepared according to the cold ethanol fractionation process (Cohn E. et al., *J. Am. Chem. Soc.,* 68:459, 1946) developed by Cohn and Oncley or the modified cold ethanol fractionation process (Kistler P, Nitschmann H S, *Vox Sang,* 7:414. 1952) developed by Kistler and Nitschmann.

However, immunoglobulins for intramuscular injection have the following problems: 1) the doses of such immunoglobulins are limited, making it impossible to administer the immunoglobulins in large amounts; 2) the immunoglobulins cause pain at the site injected with the immunoglobulins; 3) the immunoglobulins have a low content of natural immunoglobulin G (IgG) having antibody activity; 4) the antibody activity of the immunoglobulins is reduced by protease at the injected site; and 5) the time taken to reach peak blood concentrations is 24 hours or more.

In order to solve the problems of intramuscular injection, administration of immunoglobulins by intravenous injection was attempted. However, when immunoglobulin preparations were administered intravenously, a variety of immediate side effects, including difficult breathing and circulatory system shock, appeared due to a serious side effect (anaphylactic reaction) attributable to aggregates with anti-complementary activity. Such symptoms appeared mainly in immunoglobulin-deficient patients. Particularly, a side effect of serious hypersensitivity was observed in patients in which anti-IgA antibodies appeared.

In other words, in order to develop an intravenous formulation, impurities such as blood clotting factors (fibrinogen, albumin, prekallikrein activator (PKA) and transferrin) or immunoglobulins similar to hepatitis B immunoglobulin such as IgA and IgE should be removed, and it is necessary to increase the stability and purity.

Thus, as intravenous injection of immunoglobulins is impossible due to the above-described problems, development of immunoglobulin preparations for intravenous injection has been required, and methods capable of removing the above-described aggregates and/or preventing aggregate formation during preparation processes have been developed. Intravenous injection of immunoglobulins has become possible as a result of treating immunoglobulins with proteases such as pepsin, papain or Plasmin, or chemical substances such as β-propiolactone, to change their structure so as to suppress the formation of immunoglobulin aggregates or destroy immunoglobulin aggregates, thereby reducing the anti-complementary activities of the immunoglobulins.

The first-generation intravenous immunoglobulin (IVIG) products were prepared by treating a starting material (Cohn fraction II) with pepsin to remove immunoglobulin aggregates. The preparation process did not comprise a column chromatography step, and the prepared product was lyophilized so as to be stably maintained over a suitable period of time, and was dissolved immediately before use. However, it was found that IVIG products manufactured by some manufacturers caused viral infections such as viral hepatitis C. For this reason, one or more steps of inactivating and/or removing known virus were added to the preparation process. Thereafter, the second-generation IVIG products with low anti-complementary activity and higher stability were disclosed in the mid-1980s, and the IVIG products were purified by several chromatography steps.

Such preparations were injected intravenously, and thus overcame the disadvantages of intramuscular immunoglobulins, including limited dose, pain at the injected site, and the reduction in antibody of immunoglobulins by protease, and the time taken to reach peak blood concentrations was also reduced to several hours or less.

However, the intravenous immunoglobulin products as described above have little or no natural IgG with antibody activity due to their structural change, and thus have reduced or no complement binding ability and also have a blood half-life as short as about 4-12 days, suggesting that they exhibit no satisfactory effects on the prevention and treatment of diseases. Furthermore, the first-generation and second-generation IVIG products prepared in the form of lyophilized powder require an additional process for dissolving them, and have low dissolution rates. For this reason, liquid IVIG products have been developed, and improved processes have been required to obtain more stable and pure IVIG products.

In connection with this, German Patent No. 2,604,759 and U.S. Pat. No. 4,124,576 discloses methods of obtaining pure IgG (third-generation IVIG) with antibody activity by using a non-ionic surfactant such as polyethylene glycol, unlike the above-described gamma-immunoglobulin for intravenous injection. Such IgG preparations have complement binding ability and increased blood half-lives, and thus can show good effects on the prevention and treatment of diseases. However, these preparations produced by treatment with polyethylene glycol can still cause side effects, because it is difficult to completely remove aggregates with anti-complementary activity from these preparations (showing an anti-complementary activity of about 0.02 U/mg).

In addition, Korean Patent No. 1983-0007083 discloses a method of preparing an intravenous immunoglobulin from Cohn fraction II or fraction II+III, isolated from human plasma, by treatment with polyethylene glycol. However, there are problems in that the process is complicated and the yield is low.

Meanwhile, hepatitis B virus (HBV) is a virus with a DNA genome, which belongs to the Hepadnaviridae family and causes acute and chronic hepatitis. Hepatitis B virus (HBV) is classified into eight genotypes having a difference of about 8% or more in the gene nucleotide sequence, or it is classified into four serotypes (adw, adr, ayw and ayr, etc.) based on the two antigenic determinants (d/y and w/r) of hepatitis B surface antigen (HBsAg). About 3.5 hundred million people worldwide have chronic hepatitis B virus (HBV) infection. Particularly, in Korea and China, people with chronic hepatitis B virus infection reach about 5-8%, and hepatitis B virus (HBV) infection is the major cause of liver disease and liver cancer. Currently developed vaccines can be somewhat effective in the prevention of hepatitis B virus infection, but a significant number of patients with chronic hepatitis B virus infection still exist. Chronic infection with hepatitis B virus (HBV) causes hepatitis, cirrhosis and liver cancer, and the incidence of liver cancer is about 300 times higher in people with chronic hepatitis B virus infection than in non-infected people. According to the WHO report, about 80% of liver cancer is caused by chronic hepatitis B.

Currently known therapeutic agents for hepatitis B include the nucleoside analogues including lamivudine and adefovir dipivoxil, which inhibit the DNA replication of hepatitis B virus (HBV) by inhibiting the reverse transcriptase of hepatitis B virus polymerase (HBV polymerase). However, when these drugs are administered for 3 years, drug-resistant virus occurs in about 75% of the patients, thereby reducing the therapeutic effect of the drug. Due to this problem, it is impossible to treat hepatitis B infection using the viral replication inhibitors alone. For this reason, it was attempted to use these inhibitors in combination with interferon agents, but these inhibitors are not currently used due to serious side effects.

For a similar therapeutic purpose, a hepatitis B immune globulin (HBIG) preparation comprising a hepatitis B virus (HBV) antibody isolated and purified from blood having a high antibody titer was taken into consideration. However, because the antibody of the HBIG preparation is isolated and purified from plasma, there are problems, including difficulty in obtaining plasma, the possibility of viral infection, low activity, high costs and the like.

The present inventors have made extensive efforts to solve the above-described problems occurring in the prior art, and as a result, have found that thrombogenic substances in plasma fraction are effectively removed and the stability of an immunoglobulin product is improved, by dialyzing and concentrating fraction II isolated from plasma, and then purifying the fraction by anion exchange chromatography and cation exchange chromatography while controlling the salt concentration during cation exchange chromatography and elution, thereby completing the present invention.

DISCLOSURE OF INVENTION

Technical Problem

It is an object of the present invention to provide a method for preparing a human plasma-derived hepatitis B immunoglobulin preparation with high purity and stability.

Technical Solution

To achieve the above object, the present invention provides a method for preparing a human plasma-derived hepatitis B immunoglobulin preparation, comprising the steps of:
(a) dissolving plasma protein fraction II containing human plasma-derived hepatitis B immunoglobulin, collected from a healthy donor who suffered from hepatitis B or who was additionally immunized with a hepatitis B vaccine, and then obtaining a fraction II solution by filtration;
(b) dialyzing and/or concentrating the obtained fraction II solution, subjecting the dialyzed and/or concentrated solution to anion exchange chromatography, and then recovering a fraction not attached to a column used to perform the anion exchange chromatography;
(c) treating the recovered fraction with a solvent and/or a detergent to inactivate viruses, and subjecting the treated fraction to cation exchange chromatography to remove the solvent and/or the detergent, and thrombotic substances;
(d) dialyzing and/or concentrating an eluate obtained from the cation exchange chromatography; and
(e) filtering the dialyzed and/or concentrated solution, thereby obtaining a human hepatitis B immunoglobulin.

The method may further comprise, after step (e), a step of adding a stabilizer to the human hepatitis B immunoglobulin, and then adjusting the titer of the immunoglobulin, followed by bacterial filtration.

BRIEF DESCRIPTION OF THE DRAWINGS

FIG. 2 shows the results of analyzing ion exchange chromatography eluates in order to optimize the sequence and conditions of ion exchange chromatography steps in the present invention.

BEST MODE FOR CARRYING OUT THE INVENTION

Figure 1:
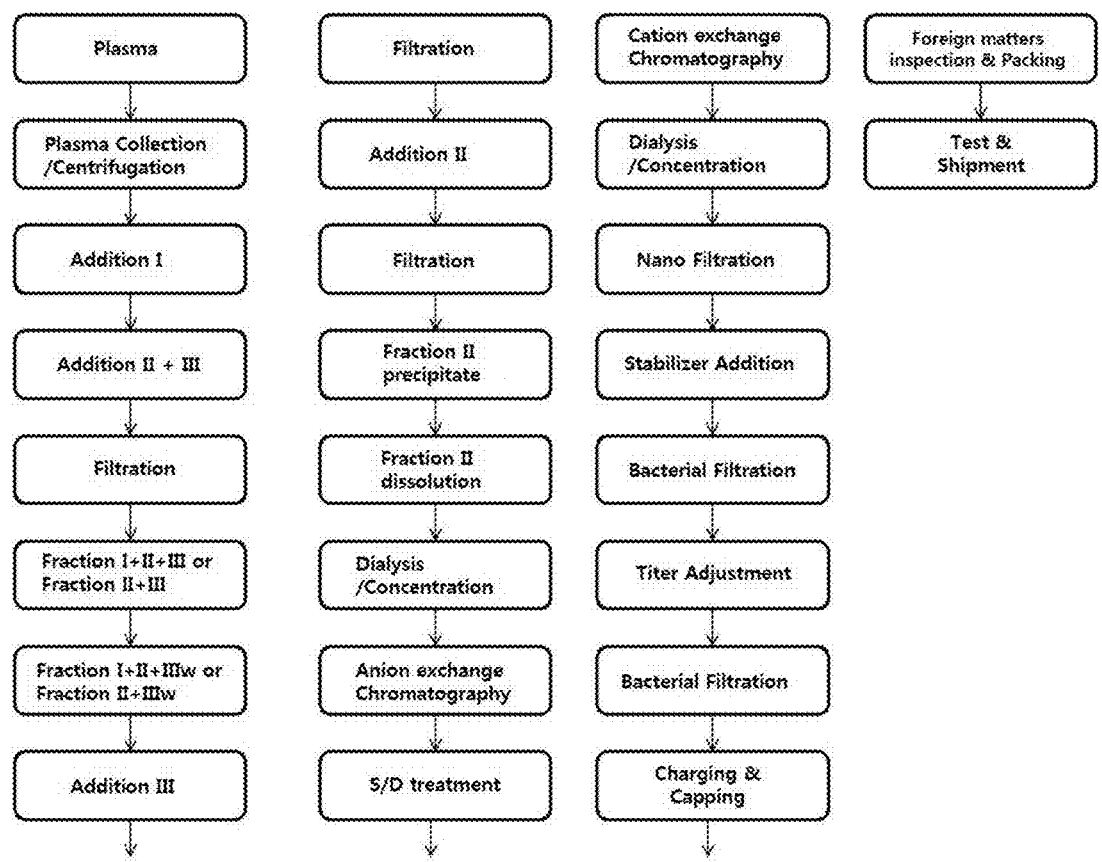
FIG. 1 is a schematic diagram showing a process for preparing a human plasma-derived hepatitis B immunoglobulin preparation for intravenous injection according to the present invention.

Unless defined otherwise, all technical and scientific terms used herein have the same meaning as commonly understood by one of ordinary skill in the art to which the invention pertains. Generally, the nomenclature used herein and the experiment methods, which will be described below, are those well-known and commonly employed in the art.

As used herein, the term "human plasma-derived hepatitis B immunoglobulin" refers to human hepatitis B immunoglobulin. Specifically, it is a human hepatitis B immunoglobulin prepared from anti-hepatitis B immunoglobulin G-containing plasma collected from a healthy donor who suffered from hepatitis B or who was additionally immunized with a hepatitis B vaccine for the purpose of producing a plasma fraction preparation. The human hepatitis B immunoglobulin may preferably be Hepavic, but is not limited thereto.

As used herein, the expression "human plasma-derived hepatitis B immunoglobulin-containing plasma protein" is meant to encompass cryoprecipitate-free plasma obtained by removing various plasma proteins such as Factor IX and antithrombin from human plasma or human placental plasma, various Cohn fractions, and fractions obtained by ammonium sulfate or PEG (Polson et al., *Biochem Biophys Acta,* 82:463, 1964); Polson and Ruiz-Bravo, *Vox Sang,* 23:107. 1972) precipitation. Preferably, the plasma protein fraction that is used in the present invention may be Cohn fraction II. Cohn fraction I, II and III or Cohn fraction II+III.

In the present invention, fraction II obtained from human plasma according to a conventional Cohn plasma fraction method was used. A subsequent purification process for removing various lipoproteins, fibrinogens, α-globulin, β-globulin and various coagulation factors from fraction II was performed.

In the present invention, human plasma is preferably obtained by performing an additional immunization on a health person with hepatitis B vaccine to increase the level of anti-hepatitis B immunoglobulin G in the plasma, and then freezing only a plasma portion collected through apheresis for the purpose of using the human plasma as a material for the preparation of plasma fraction preparations. The human plasma used was subjected to Biotests, including nucleic acid amplification tests on human immunodeficiency virus (HIV), hepatitis C virus (HCV), and hepatitis B virus (HBV), and serological tests. The plasma stored at −20° C. or below was thawed by incubation in a jacketed vessel at 1 to 6° C. for 12-72 hours.

While the plasma was thawed under the above-described conditions, a cryoprecipitate including fibrinogen and coagulation factors was produced. The produced cryoprecipitate was removed by centrifugation, and the remaining cryo-poor plasma was recovered. Then, precipitation and filtration processes were repeated, thereby obtaining fraction II.

In the filtration process for isolating human plasma-derived hepatitis B immunoglobulin-containing plasma, a filter aid was added to and mixed with the cryo-poor plasma which was then separated into a supernatant and a precipitate by means of a filter press. As the filter aid, Celite (STD), Harbolite (Expanded perlite product) or the like was used.

In the present invention, the dissolving of the plasma protein fraction II in step (a) may be performed by adding a sodium chloride solution in an amount equivalent to 2-10 times the volume of the plasma protein fraction.

The plasma protein fraction is preferably suspended (dissolved) in water and/or buffer at a substantially non-denaturing temperature and pH. The term "substantially non-denaturing" implies that the condition to which the term refers does not cause substantial irreversible loss of functional activity of the immunoglobulin molecules, e.g. loss of antigen binding activity and/or loss of biological Fc-function.

Advantageously, the plasma protein fraction is dissolved in water acidified with at least one non-denaturing buffer at volumes of from 2 to 10, preferably from 3 to 5, times that of the plasma protein fraction. The pH of the human hepatitis B immunoglobulin-containing suspension is preferably maintained at a pH below 6.0, preferably 4.0-6.0, more preferably 4.5-5.5, most preferably 4.8-5.2, in order to ensure optimal solubility of the human hepatitis B immunoglobulin. Any acidic buffer known in the art can be used, but sodium phosphate, sodium acetate, sodium chloride, acetic acid, hydrochloric acid, or water (distilled water) may preferably used as the acidic buffer. In the present invention, sodium chloride solution was used.

The human plasma-derived hepatitis B immunoglobulin suspension is maintained at a low temperature so as to prevent protein denaturation and minimize protease activity, and the human plasma-derived hepatitis B immunoglobulin suspension, and water or buffer added to the immunoglobulin suspension, are maintained at a temperature ranging from −12 to 10° C., preferably from −12 to 0° C., more preferably from −12 to −8° C.

In the present invention, the filtration in step (a) that is a step of obtaining the fraction II solution may be clarifying filtration, and may comprise adjusting pH to 4.5-5.5. Preferably, the pH is adjusted to 4.8-5.2.

In the present invention, the fraction II was transferred into a jacketed vessel at 10° C. or below, and dissolved by adding thereto a 0.6% sodium chloride solution in an amount of 4 times equivalent to the volume of the fraction II, and then 1M acetic acid was added to the solution to adjust the pH to 5.0±0.2. Next, the solution was subjected to clarifying filtration using a depth filter cartridge, thereby obtaining a fraction II solution.

In the present invention, the dialysis and/or concentration in step (b) may be performed using an ultrafiltration/diafiltration (UF/DF) system until the osmotic pressure of the dialyzed and concentrated solution reaches 10 mOsmol/kg or lower, followed by adjusting the pH to 5.5-6.5, preferably 5.95-6.35.

Diafiltration is a process of removing only a certain solute from a fluid containing a solvent and two or more solutes having different molecular sizes by simultaneously performing dialysis and ultrafiltration. It is effective for purification of polymer materials and has advantages over general dialysis processes in that it is time-saving and cost-effective.

In an example of the present invention, the fraction II solution was filtered using an ultrafiltration/diafiltration (UF/DF) system at an osmotic of 10 mOsmol/kg or lower, and 1M sodium acetate was added to the filtrate to a concentration of 5.0±1.0 mM, followed by adjusting the pH to 6.15±0.20, thereby obtaining a dialyzed and/or concentrated, human plasma-derived hepatitis B immunoglobulin-containing solution.

In the present invention, the anion exchange chromatography in step (b) may be performed at a pH of 5.5-7.0, preferably 6.15±0.20 and a flow rate of 30-150 cm/hr, and a fraction not attached to the anion exchange chromatography column may be recovered with 1.0-2.0 loading volumes (LV).

The anion exchange resin that is used in the anion-exchange chromatography step may be a diethylaminoethyl (DEAE)-based anion exchange resin. Herein, an anion exchange resin substituted with quaternary ammonium groups can be used, but is not limited thereto. Preferably, the anion exchange resin may be any one selected from among anion exchange resins having a strongly basic quaternary ammonium group or a weakly basic diethylaminoethyl (DEAE) group.

For example, as a strongly basic anion exchange resin, Q Sepharose Fast Flow, Q Sepharose High Performance, Resource Q, Source 15Q, Source 30Q, Mono Q, Mini Q, Capto Q, Capto Q ImpRes, Q HyperCel, Q Cermic HyperD F, Nuvia Q, UNOsphere Q, Macro-Prep High Q, Macro-Prep 25 Q, Fractogel EMD TMAE(S), Fractogel EMD TMAE Hicap (M), Fractogel EMD TMAE (M), Eshmono Q, Toyopearl QAE-550C, Toyopearl SuperQ-650C, Toyopearl GigaCap Q-650M, Toyopearl Q-600C AR, Toyopearl SuperQ-650M, Toyopearl SuperQ-650S, TSKgel SuperQ-5PW (30), TSKgel SuperQ-5PW (20), TSKgel SuperQ-5PW or the like may be used, but is not limited thereto, and any anion exchange resin known in the art may be used.

The appropriate volume of resin used in the anion exchange chromatography is reflected by the dimensions of the column, i.e., the diameter of the column and the height of the resin, and varies depending on, for example, the amount of the human plasma-derived hepatitis B immunoglobulin in the applied solution and the binding capacity of the resin used. Before performing ion exchange chromatography, the ion exchange resin is preferably equilibrated with a buffer which allows the resin to bind its counterions.

In the present invention, the anion exchange resin used is DEAE Sepharose gel, and the column buffers used may be equilibration buffer known in the art, for example, sodium phosphate buffer, citrate buffer, acetate buffer or the like, wash buffer and elution buffer.

In the anion exchange chromatography, the column was equilibrated with 10 mM buffer, preferably sodium phosphate buffer or sodium acetate buffer such that the pH would be 5.5-7.0, preferably 6.15±0.2, and the flow rate of the mobile phase was controlled to 30-150 cm/hr. The fraction not attached to the anion exchange chromatography column was recovered with 1.0-2.0 loading volumes (LV).

In the present invention, the anion exchange chromatography of step (b) may recover a non-adsorbed solution.

In the present invention, step (c) is a step of inactivating viruses such as potential lipid enveloped viruses in the human plasma-derived hepatitis B immunoglobulin-containing solution and then removing a substance used for the inactivation. In this step, a virus-inactivating agent, preferably a solvent and/or a detergent, may be used. Most preferably, solvent & detergent treatment employing a solvent-detergent mixture may be used.

Through step (c), lipid enveloped viruses (e.g. HIV1 and HIV2, hepatitis type C and non A-B-C, HTLV 1 and 2, the herpes virus family, CMV and Epstein Barr virus, etc.) can be inactivated, and thus the safety of the final product can be increased.

In step (c), any solvent and detergent may be used without any limitation, as long as they have the capability to inactivate viruses, particularly lipid enveloped viruses. The detergent may be selected from the group consisting of non-ionic and ionic detergents and is preferably selected to be substantially non-denaturing. Particularly, a non-ionic detergent is preferable in terms of easy removal. The solvent is most preferably tri-n-butyl phosphate (TNBP) as disclosed in U.S. Pat. No. 4,764,369, but is not limited thereto.

Particularly preferred virus-inactivating agents for carrying out the invention are mixtures of TNBP and one or more agent selected form the group consisting of polysorbate 80 (Tween 80), Triton X-100 and Triton X-45, but is not limited thereto.

The preferred solvent/detergent mixture is added such that the concentration of TNBP in the human plasma-derived hepatitis B immunoglobulin-containing solution is 0.2-0.6 wt %, preferably 0.24-0.36 wt %, and such that the concentration of Tween 80 is 0.8-1.5 wt %, preferably 0.8-1.2 wt %.

The virus-inactivation step is performed under conditions that inactivate enveloped viruses, resulting in a substantially virus-safe, human plasma-derived hepatitis B immunoglobulin-containing solution. Such conditions include a temperature of 4-30° C., preferably 19-28° C., most preferably 24-26° C., and an incubation time of 1-24 hours, preferably 4-12 hours, most preferably about 8 hours, to ensure sufficient virus inactivation.

In the present invention, the cation-exchange chromatography in step (c) may be performed at a pH of 5.0-6.5, preferably 5.6-6.0. After adsorption of the human plasma-derived hepatitis B immunoglobulin, washing with equilibration buffer is performed. The equilibration buffer that is used in the washing may be used in an amount of at least three times the column volume, preferably at least five times the column volume. After washing, the human hepatitis B immunoglobulin is eluted with elution buffer having at least 0.5-1.5 times the adsorption volume.

The cation exchange resin that is used in the present invention may be a Sephardex-based cation exchange resin, Sepharose-based cation exchange resin, HyperCell or Source, but is not limited thereto, and other cation exchange resins known in the art may also be used. In the present invention, a Sephardex-based cation exchange resin may preferably be used. In an example of the present invention, CM Sephardex gel that is a ceramic-based resin was used as the cation exchange resin, and equilibration buffer known in the art, such as sodium phosphate buffer, citrate buffer or acetate buffer, wash buffer and elution buffer were used as the column buffers.

The elution of the human plasma-derived hepatitis B immunoglobulin from the cation exchange resin is performed with a substantially non-denaturing buffer having a pH and ionic strength sufficient to cause efficient elution of the human hepatitis B immunoglobulin, thereby recovering a human plasma-derived hepatitis B immunoglobulin-containing eluate. Herein, "efficient elution" means that at least 75%, such as at least 80%, for example, at least 85%, of the human plasma-derived hepatitis B immunoglobulin solution loaded onto the cation exchange resin is eluted from the cation exchange resin.

In the present invention, the cation exchange chromatography in step (c) may be performed at the salt concentration of the eluting buffer, which is sufficiently high to displace the human plasma-derived hepatitis B immunoglobulin from the cation exchange resin. It may be performed at a salt concentration of 500-1,500 mM, preferably 800-1,200 mM.

In the present invention, the dialysis and/or concentration in step (d) may be performed using an ultrafiltration/diafiltration (UF/DF) system. It is performed at an osmotic pressure of 10 mOsmol/kg or lower and a pH of 3.5-4.5, preferably 3.8±0.2.

In the present invention, diafiltration was performed in order to remove low-molecular ions from the cation exchange chromatography eluate, and the osmotic pressure in the UF/DF system was maintained at 10 mOsmol/kg or less. Thereafter, hydrochloric acid was added to the filtrate to adjust the pH to 3.8±0.2.

In the present invention, the filtration in step (e) may be performed at a pressure of 1.5-2.5 bar using a nanofiltration system.

The method of the present invention may further comprise, after step (e), a step of adding a stabilizer to prepare an human plasma-derived hepatitis B immunoglobulin for intravenous injection.

After completion of the nanofiltration, at least one protein stabilizer known in the art may be added, and examples thereof include various sugar alcohols and saccharides (such as sorbitol, mannose, trehalose, maltose), proteins (such as albumin), amino acids (such as lysine, glycine, etc.) and organic agents (such as PEG and Tween 80).

In the present invention, after step (e), a stabilizer that can be added may be at least one selected from among sugar alcohol, maltose, sorbitol, mannose, glucose, trehalose, albumin, lysine, glycine, PEG and Tween 80. Preferably, maltose is used as the stabilizer.

The stabilizer may be added to a final concentration of 90-110 g/l. After addition of the stabilizer, the pH of the immunoglobulin solution may be adjusted to 3.5-4.5. Preferably, the pH may be adjusted to 3.6-4.0 by adding an acid, preferably sulfuric acid or hydrochloric acid.

Nanofiltration is an important virus-removing step. In the present invention, the dialyzed and concentrated human plasma-derived hepatitis B immunoglobulin solution was filtered through a Pall DVD pre-filter and a DV20 virus filter at a pressure of 2.0±0.5 bar to remove viruses from the human plasma-derived hepatitis B immunoglobulin solution. Then, maltose was added to the nanofiltered solution to a final concentration of 90-110 g/l to stabilize the human plasma-derived hepatitis B immunoglobulin. The stabilized, human plasma-derived hepatitis B immunoglobulin solution was adjusted to a pH of 3.0-4.6, preferably 3.6-4.0 by addition of hydrochloric acid. Then, it was sterilized using a 0.2 μm filter and stored.

The sterilized, human plasma-derived hepatitis B immunoglobulin preparation for intravenous injection may be diluted or concentrated such that the concentration of the protein (purified, human plasma-derived hepatitis B immunoglobulin) is 1-20 wt %. In the present invention, the sterilized immunoglobulin preparation was diluted with WFI or concentrated by ultrafiltration such that the protein concentration would be 40-60 g/l, preferably 45-55 g/l, more preferably 49.5-50.5 g/l. Then, the titer of the immunoglobulin preparation was adjusted to 200 IU/mL or higher, and then maltose was added to the immunoglobulin solution to reach a final concentration of 90-110 g/l and thoroughly mixed, and then the pH of the stabilized, human plasma-derived hepatitis B immunoglobulin preparation was measured, and hydrochloric acid was added to the immunoglobulin solution to adjust the pH to 4.2±0.2, thereby preparing a human plasma-derived hepatitis B immunoglobulin preparation for intravenous injection.

In an example of the present invention, the concentration of impurities (blood coagulation factors (e.g., fibrinogen, albumin, prekallikrein activator (PKA) and transferrin, etc.) and hepatitis B immunoglobulin-like protein (IgA and IgE)) in a filtrate or precipitate in each preparation step were measured. As a result, it could be seen that the impurities were mostly removed through the purification process (Table 1 and Table 2).

EXAMPLES

Hereinafter, the present invention will be described in further detail with reference to examples. It will be obvious to a person having ordinary skill in the art that these examples are for illustrative purposes only and are not to be construed to limit the scope of the present invention.

Example 1: Preparation of Human Hepatitis B Immunoglobulin Preparation for Intravenous Injection 1-1: Preparation of Plasma As plasma, FDA-approved plasma was used which was subjected to Biotests, including nucleic acid amplification tests on human immunodeficiency virus (HIV), hepatitis C virus (HCV), and hepatitis B virus (HBV), and serological tests.

In the present invention, plasma (Batch No. 600A9008) obtained from the Red Cross was used. The plasma was stored at −20° C. or below until use. A bottle containing the plasma was opened with a bottle cutting machine, and the plasma was thawed by incubation in a jacketed vessel at 1-6° C. for 12-72 hours.

While the plasma was thawed under the above-described conditions, a cryoprecipitate containing fibrinogen and coagulation factors was produced. The produced cryoprecipitate was removed by centrifugation (description of conditions), and the remaining cryo-poor plasma was recovered.

1-2: Precipitation I Step

To additionally remove coagulation factors from the cryo-free plasma, a precipitation I step was performed.

96% ethanol was added to the cryo-poor plasma recovered in Example 1-1 such that the final ethanol concentration would be 8±0.8% at −3±1° C. (addition I), and then the pH of the solution was adjusted to a 7.2±0.2 using acetate buffer. The precipitate was removed by centrifugation, and the supernatant (addition I supernatant) was recovered. For total viable count, a portion of the supernatant was sampled and stored.

1-3: Precipitation II+III Step and Filtration

To precipitate a human plasma-derived hepatitis B immunoglobulin (Hepabig, HBIG) contained in the supernatant recovered in Example 1-2, a precipitation II+III step was performed.

To the cryo-poor plasma subjected to the precipitation I step, 96% ethanol was additionally added the supernatant recovered in Example 1-2 such that the final ethanol concentration would be 20±2% at −5±1.0° C. (addition II+III). Then, the pH of the solution was adjusted to 6.9±0.1 using acetate buffer.

Next, a filter aid (Celite(STD) or Harbolite(Expanded perlite product)) was added to the solution in an amount of 0.0284 kg per kg of the plasma and mixed for 30±10 minutes. The mixture was separated into a supernatant and a precipitate on a filter press (DG800K) in a cold room maintained at a temperature of 2 to 8° C.

The supernatant was named "supernatant I+II+III (or II+III)", and the precipitate was named "fraction I+II+IIIw (or II+IIIw)" (w; wash). Fraction I+II+IIIw (or II+IIIw) was immediately used or was stored at −20° C. or below.

1-4: Precipitation III Step and Filtration

To additionally remove albumin, lipoprotein, thrombin and other unwanted proteins from human plasma-derived hepatitis B immunoglobulin-containing fraction I+II+IIIw (or II+IIIw), a precipitation III step was performed.

The fraction I+II+IIIw (or II+IIIw) recovered in Example 1-3 was dissolved in cold distilled water, and a portion of the solution was sampled and stored for total viable count. Then, 96% ethanol was added to the dissolved fraction I+II+IIIw (or II+IIIw) such that the final ethanol concentration would be 18±1.8% at −5±1.0° C. (addition III). Next, the solution was adjusted to a pH of 5.2±0.1 by addition of an acetate buffer prepared at −6° C.

Next, the mixture was separated into a supernatant and a precipitate by means of a filter press (DG800K). The supernatant was named "filtrate I+III (or III)", and the precipitate was named "fraction I+III (or III)". Fraction I+III (or III) was discarded, and a portion of filtrate I+III (or III) was sampled and stored for total viable count.

1-5: Precipitation II Step and Filtration

To precipitate the human hepatitis B immunoglobulin in filtrate I+III (or III) obtained in Example 1-4, a precipitation II step was performed.

96% ethanol was added to filtrate I+III (or III) such that the final ethanol concentration would be 25±2.5% at −10±2.0° C. Next, the solution was adjusted to a pH of 7.4±0.2 by addition of 1M sodium bicarbonate.

Then, the mixture was separated into a supernatant and a precipitate by means of a filter press (DG800K). The precipitate was named "fraction II paste", and a portion of the precipitate was sampled and stored for measurement of the contents of bacterial endotoxin and protein and the composition thereof.

1-6: Fraction II Dissolution and Clarifying Filtration

Isolation/purification processes for increasing the content of the human plasma-derived hepatitis B immunoglobulin isolated from the plasma and removing thrombotic substances were performed.

First, the human hepatitis B immunoglobulin-containing fraction II paste isolated in Example 1-5 was dissolved to have conditions suitable for dialysis. The fraction II was transferred into a jacketed vessel at 10° C. or lower and dissolved by adding thereto a 0.6% sodium chloride solution in an amount equivalent to 4 times the volume of the fraction II, and a portion of the solution was sampled and stored in order to measure the protein content and composition thereof.

Next, the solution was adjusted to a pH of 5.0±0.2 by addition of 1M acetic acid, and then the solution was subjected to clarifying filtration using depth filter cartridges (BecodiskBP01), thereby obtaining a fraction II solution.

1-7: Diafiltration

The human hepatitis B immunoglobulin-containing fraction II solution obtained in Example 1-6 was diafiltered to remove ethanol and low-molecular-weight ions, and the pH thereof was adjusted so that the solution would have conditions suitable for anion exchange chromatography.

The human hepatitis B immunoglobulin-containing fraction II solution was diafiltered using an ultrafiltration/diafiltration system (Millipore Pellicon2 (50K)) at an osmotic pressure of 10 mOsmol/kg or lower, and a portion of the obtained filtrate was sampled and stored in order to measure the protein content and composition thereof and count viable cells.

The filtrate was adjusted to a pH of 6.15±0.2 by adding 0.5 M sodium phosphate such that the concentration there of would be 10.0±1.0 mM, thereby obtaining a dialyzed and/or concentrated human hepatitis B immunoglobulin solution.

1-8: Anion Exchange Chromatography

In order to remove polymer and other plasma proteins from the dialyzed and/or concentrated human hepatitis B immunoglobulin solution obtained in Example 1-7, anion exchange chromatography was performed.

The anion exchange resin DEAE-Sepharose gel (GE Healthcare, Catalog No. 17-0709) was packed into a column, and then equilibrated with equilibration buffer such that the pH would be 6.15±0.2. Next, the dialyzed and/or concentrated human hepatitis B immunoglobulin solution obtained in Example 1-7 was loaded into the column at a flow rate of 50±10 cm/hr. Next, a fraction not attached to the anion exchange chromatography column was recovered with 1.5 loading volume (LV).

1-9: Solvent/Detergent Treatment for Virus Inactivation

To inactivate potential lipid enveloped viruses in the human hepatitis B immunoglobulin-containing solution, a step of treating the solution with a solvent and a detergent was performed.

First, hydrochloric acid (HCl) or sodium hydroxide (NaOH) was added to the fraction not attached to the anion exchange chromatography column and recovered in Example 1-8, such that the pH of the fraction would be 5.0±0.2. Then, tri(n-butyl)-phosphate (TNBP) and polysorbate 80 (Tween 80) were added to the fraction such that concentrations thereof would be 0.3±0.06% and 1±0.2%, respectively, followed by stirring at 200±50 RPM for 20-30 minutes. In order to whether TNBP and Tween 80 in the solution were uniformly mixed, a portion of the solution was sampled and confirmed. Thereafter, the solution was continuously stirred at 25±1.0° C. and 200±50 RPM for 8 hours. The human hepatitis B immunoglobulin-containing solution was transferred to another tank (that is a viral secure area (VSA)) through a hard pipeline.

1-10: Cation Exchange Chromatography

To remove TNBP, Tween 80 and other thrombotic substances such as coagulation factors from the human hepatitis B immunoglobulin solution treated with the solvent/detergent, cation exchange chromatography was performed.

The cation exchange resin CM-Sephadex C-50 (GE Healthcare) was packed into a column, and then equilibrated with equilibration buffer such that the pH would be 5.8±0.2.

Next, the human hepatitis B immunoglobulin solution treated with the solvent/detergent in Example 1-9 was adsorbed for 3±1 hours. Thereafter, after washing seven times using wash buffer having 2-3 times the adsorption volume, the human hepatitis B immunoglobulin was eluted with elution buffer (elution buffer composition: 1.0 M NaCl) and recovered.

1-11: Diafiltration

To remove low-molecular-weight ions from the cation exchange chromatography eluate, diafiltration was performed.

The eluate obtained in Example 1-10 was diafiltered using an ultrafiltration/diafiltration system (Millipore Pellicon2 (50K)) at an osmotic pressure of 10 mOsmol/kg or lower. In order to maintain the immunoglobulin polymer content, the cation exchange chromatography eluate was added to the calculated dialysate concentrate, and the ultrafiltration/diafiltration (UF/DF) was continuously performed while a sodium chloride concentration of 100 mM or lower was maintained.

A portion of the obtained filtrate was sampled and stored in order to measure the protein content and composition thereof and count viable cells, and the remaining filtrate was adjusted to a pH of 4.2±0.2 by addition of hydrochloric acid (HCl).

1-12: Nanofiltration and Addition of Stabilizer

Nanofiltration is an important virus-removing step. The dialyzed/concentrated human hepatitis B immunoglobulin solution obtained in Example 1-11 was filtered through a Florodyne II prefilter (AB1DJL7PH4) and filtered through a virus filter (DV20, AB3DV207PH4) at a pressure of 2.0±0.5 bar to thereby remove viruses from the human hepatitis B immunoglobulin solution.

In order to stabilize the human hepatitis B immunoglobulin, maltose was added to the nanofiltered filtrate such that a final concentration would be 10±1 wt %, and was thoroughly mixed. Then, the pH of the stabilized human plasma-derived hepatitis B immunoglobulin solution was measured, and the human hepatitis B immunoglobulin solution was adjusted to a pH of 3.8±0.2 by addition of hydrochloric acid.

Next, the filtrate was sterilized using a 0.2 µm filter and stored in a stainless steel storage tank.

1-13: Preparation of Final Preparation of Human Hepatitis B Immunoglobulin for Intravenous Injection and Aseptic Filling The resulting human hepatitis B immunoglobulin preparation for intravenous injection was diluted with WFI or concentrated by ultrafiltration such that the protein concentration would be 50±1 g/l. Next, maltose was added thereto such that a final concentration thereof would be 10±1 wt %, and was thoroughly mixed. Then, the titer of the immunoglobulin preparation was adjusted to 200 IU/mL or higher. Thereafter, the pH of the stabilized human hepatitis B immunoglobulin preparation was measured and adjusted to a pH of 4.2±0.2 by addition of hydrochloric acid.

After pH adjustment, the human hepatitis B immunoglobulin preparation was sterilized, and transferred to a packing room to prepare a product, and was in turn stored at a temperature of 2-8° C.

Example 2: Measurement of Concentrations of Impurities Contained in the Filtrate or Precipitate Resulting from Each Preparation Step In order to examine the degree of removal of coagulants, the concentrations of fibrinogen, albumin, transferrin, IgA and IgE contained in the filtrate or precipitate resulting from each preparation step of Example 1 were measured by an ELISA kit (Assaypro, Korea), and the prekallikrein activator (PKA) activity in the filtrate or precipitate resulting from each preparation step of Example 1 was calculated by measuring the absorbance per minute at 280 nm by use of kallikrein substrate solution (S-2302. Sigma Aldrich).

TABLE 1

Impurity contents of purification process products

| Process | Remarks | Albumin (µg/mL) | Transferrin (µg/mL) | IgA (µg/mL) | IgE (µg/mL) | PKA (IU/mL) |
|---|---|---|---|---|---|---|
| Anion exchange chromatography (AEX) | Loaded solution | 132.112 | 377.897 | 132.03 | 0.491 | 10.71 |
| | Collected solution | 0.486 | 8.148 | 16.21 | <0.016 | <2.00 |
| | Impurity LRV (−log removal value) | 2.26 | 1.49 | 0.73 | >1.31 | — |

TABLE 2

Impurity contents of purification process products

| Process | Remarks | Fibrinogen (µg/mL) |
|---|---|---|
| Cation exchange chromatography (CEX) | Loaded solution | 0.69 |
| | Concentrate after collection | <0.165 |
| | Impurity LRV (−log removal value) | >0.94 |

Regarding the purification efficiency in Tables 1 and 2 above, PKA is a factor that enables whether or not impurities such as factor 12 would be removed, by measuring the activity of prekallikrein remaining after prekallikrein is converted to kallikrein by activation with materials such as factor 12. PKA is expressed in units of IU/ml. LRV refers to the log removal value of the corresponding impurity, and is arithmetically calculated using the following equation: −log ((collected solution×impurity content (mg) per ml)/(loaded solution×impurity content (mg) per ml)).

The contents of impurities (fibrinogen, albumin, transferrin, PKA, IgA and IgE) in the purification process products obtained in the present invention were measured. As a result, as can be seen in Tables 1 and 2 above, the impurity concentrations started to decrease from the anion exchange resin chromatography process. In the cation exchange resin chromatography eluate, the impurities were detected at very low concentrations. Particularly, fibrinogen, albumin, transferrin, PKA, IgA and IgE were mostly removed through the chromatography purification processes.

Example 3: Optimization of Chromatography Conditions

In order to optimize the sequence and conditions of ion exchange chromatography steps, the sequence and conditions of the chromatography steps of Example 1 were controlled as shown in FIG. 2. The concentrations of fibrinogen, albumin, transferrin and IgE in the chromatography eluates were measured by an ELISA kit (Assaypro, Korea), and prekallikrein activator (PKA) activity was calculated by measuring the absorbance per minute at 280 nm by use of kallikrein substrate solution (S-2302. Sigma Aldrich).

As a result, as can be seen in FIG. 2, a method comprising performing anion exchange chromatography at pH 6.15 and then performing cation exchange chromatography, as described in Example 1, showed the highest efficiency and the lowest impurity concentration.

Although the present invention has been described in detail with reference to the specific features, it will be apparent to those skilled in the art that this description is only for a preferred embodiment and does not limit the scope of the present invention. Thus, the substantial scope of the present invention will be defined by the appended claims and equivalents thereof.

INDUSTRIAL APPLICABILITY

When the preparation method of the human plasma-derived hepatitis B immunoglobulin preparation according to the present invention is used, the efficiency with which impurities and thrombotic substances are removed can be increased and the polymer content can be maintained, and thus a human plasma-derived hepatitis B immunoglobulin with stable and improved quality can be produced.

The invention claimed is:
1. A method for preparing a human plasma-derived hepatitis B immunoglobulin preparation, comprising the steps of:
  (a) dissolving a plasma protein fraction II containing human plasma-derived hepatitis B immunoglobulin, collected from a healthy donor who suffered from hepatitis B or who was additionally immunized with a hepatitis B vaccine, and then obtaining a fraction II solution by filtration;
  (b) dialyzing and/or concentrating the fraction II solution obtained in (a), subjecting the dialyzed and/or concentrated solution to anion exchange chromatography under pH of 5.95 to 6.35, and then recovering a fraction not attached to a column used to perform the anion exchange chromatography;
  (c) treating the recovered fraction of (b) with a solvent and/or a detergent to inactivate viruses, and subjecting the treated fraction to cation exchange chromatography under pH of 5.6 to 6.0 to remove the solvent and/or the detergent, and thrombotic substances;
  (d) dialyzing and/or concentrating an eluate obtained from the cation exchange chromatography of (c);
  (e) filtering the dialyzed and/or concentrated solution of (d), thereby obtaining a human hepatitis B immunoglobulin;
  (f) adding a stabilizer to the human hepatitis B immunoglobulin of (e) to give a stabilizer-added human hepatitis B immunoglobulin solution and adjusting pH of the stabilizer-added human hepatitis B immunoglobulin solution to 3.5-4.5; and

(g) subjecting the pH adjusted immunoglobulin solution (f) to sterilization using a filter, followed by adjusting pH of the sterilized immunoglobulin solution to 4.0-4.5.

2. The method of claim 1, wherein the dissolving of the plasma protein fraction II in step (a) is performed by adding a sodium chloride solution in an amount equivalent to 2-10 times the volume of the plasma protein fraction.

3. The method of claim 1, wherein the filtration in step (a) is clarifying filtration, and is performed by adjusting pH to 4.5-5.5.

4. The method of claim 1, wherein the dialysis and/or concentration in step (b) is performed at an osmotic pressure of 10 mOsmol/kg or lower, followed by adjusting the pH to 5.5-6.5.

5. The method of claim 1, wherein the anion exchange chromatography of step (b) recovers a non-adsorbed solution.

6. The method of claim 1, wherein the anion exchange chromatography of step (b) is performed at a pH of 5.95 to 6.35, and a flow rate of 30-150 cm/hr, and the fraction not attached to the anion exchange chromatography column is recovered with 1.0-2.0 loading volumes (LV).

7. The method of claim 1, wherein the anion exchange chromatography of step (b) uses a diethylaminoethyl (DEAE)-based anion exchange resin.

8. The method of claim 1, wherein the solvent is tri(n-butyl) phosphate (TNBP), and the detergent is at least one selected from among polysorbate 80, Triton X-100, and Triton X-45.

9. The method of claim 1, wherein the cation exchange chromatography in step (c) is performed at a salt concentration of 500-1,500 mM.

10. The method of claim 1, wherein the cation-exchange chromatography in step (c) uses a Sephardex-based cation exchange resin.

11. The method of claim 1, wherein the dialysis and/or concentration in step (d) is performed at an osmotic pressure of 10 mOsmol/kg or lower.

12. The method of claim 1, wherein the filtration in step (e) is performed at a pressure of 1.5-2.5 bar using a nanofiltration system.

13. The method of claim 1, wherein the stabilizer is at least one selected from among sugar alcohol, maltose, sorbitol, mannose, glucose, trehalose, albumin, lysine, glycine, PEG and Tween 80.

14. The method of claim 1, wherein the stabilizer is added such that a final concentration is 90-110 g/l.

* * * * *